United States Patent [19]
Bullwinkel

[11] Patent Number: 6,079,829
[45] Date of Patent: Jun. 27, 2000

[54] FIBER OPTIC EYE-TRACKING SYSTEM UTILIZING OUT-OF-BAND LIGHT SOURCE

[76] Inventor: Paul E. Bullwinkel, P.O. Box 1777, Jenson Beach, Fla. 34958

[21] Appl. No.: 09/433,918

[22] Filed: Nov. 4, 1999

[51] Int. Cl.$^7$ ........................................................ A61B 3/14
[52] U.S. Cl. .............................................................. 351/210
[58] Field of Search ..................................... 351/203, 209, 351/210, 208; 359/368; 250/221

[56] References Cited

U.S. PATENT DOCUMENTS

| | | |
|---|---|---|
| 5,270,748 | 12/1993 | Katz . |
| 5,345,281 | 9/1994 | Taboada et al. . |
| 5,422,689 | 6/1995 | Knapp et al. . |
| 5,517,021 | 5/1996 | Kaufman et al. . |
| 5,583,335 | 12/1996 | Spitzer et al. . |
| 5,867,308 | 2/1999 | Pensel et al. ............................ 359/368 |

*Primary Examiner*—George Manuel
*Attorney, Agent, or Firm*—McHale & Slavin

[57] ABSTRACT

An eye tracking device for analyzing motion of an individual's eye includes an image conveyor subsystem, an image receiving subsystem, and an image processing subsystem. The image conveyor subsystem includes a flexible fiber optic image guide having a first end spaced apart from a second end by a middle portion. The image guide first and second ends are in optical communication with each other. The image guide first end is positioned at a selected location with respect to an individual's eye. The second end is interfaced with the image receiving subsystem. The image receiving subsystem includes CCD video camera. The CCD video camera converts real-time analog eye images conveyed by the fiber optic image guide into digitized representations of the eye image. The light source utilized to form the reflected images is an independent source of illumination selected from infrared light or an equivalent portion of the non-visible spectrum. These digital representations are analyzed by the image processing subsystem. The image processing subsystem includes a computer directed by included computer software. The software analyzes the digitized image and produces diagnostic feedback.

10 Claims, 2 Drawing Sheets

FIBER OPTIC EYE-TRACKING SYSTEM UTILIZING OUT-OF-BAND LIGHT SOURCE

FIELD OF THE INVENTION

This invention is directed to eye tracking devices; particularly to an eye tracking device suited for analyzing eye-movement of a patient undergoing diagnostic treatment within a magnetic resonance imaging apparatus, and most particularly to such devices which utilize an out-of-band light source.

BACKGROUND OF THE INVENTION

Monitoring of eye motion can provide a variety of information. Sleep researchers, for example, use eye motion as an indicator of various sleep stages. Also, persons with limited muscle control can use eye motion to interact with others or to control specialized equipment. Military applications that follow eye motion for targeting purposes or vehicle control have also been developed. Eye tracking devices are even used in the video game entertainment industry, where interactive environments adjust to follow the motion of a player's eyes.

Many eye tracking devices monitor muscle activity to assess eye motion. For example, U.S. Pat. No. 5,517,021 discloses an eye tracking apparatus that detects bioelectromagnetic signals generated by the muscles that move an individual's eye. The signals are analyzed and corresponding control signals are produced as output. U.S. Pat. No. 5,422,689 discloses an eye tracking device that uses sensors to monitor electro-oculogram signals produced by eye motion. The sensors are coupled with a microprocessor that analyzes this signals to determine an operator's horizontal or vertical eye movement.

Other eye tracking devices rely on changes in light patterns to track eye motion. For example, U.S. Pat. No. 5,270,748 discloses an eye tracker that uses detection devices for determining the point of regard of an operator. Included conversion circuitry determines the position of fovea-reflected light, allowing computation of an individual's visual axis and the associated point of regard. U.S. Pat. No. 5,345,281 discloses a system that uses reflected infrared light to track the gaze of an operator's eye. The U.S. Pat. No. 5,345,281 system directs infrared light towards the eye and considers differences in infrared reflectivities between the pupil, iris, and sclera to compute eye position. U.S. Pat. No. 5,583,335 discloses an eye tracking system that includes an active matrix display. Pixels in the display are aligned with corresponding photodetectors. Axial light rays from the display pixels are reflected by the eye and detected by respective photodetectors. In turn, the array of photodetectors generates an eye-position-indicating electrical signal.

Although known detectors provide certain information about eye motion, they have limitations. In many cases, simple eye motion monitoring does not provide a complete picture. For example, eye tracking devices that monitor eye-moving muscles typically do not sense pupil action. Feedback regarding pupil contraction and dilation provides important cues during diagnostic medical procedures. Devices that do not track this pupil activity do not provide enough information for many types of medical tests. Other trackers, such as those that monitor reflected light, may provide some information about pupil action, but do not provide real-time visual images of the eye, itself. Without this visual image to provide context, electrical eye-position information may be hard to interpret and almost impossible to cross reference. Prior U.S. Pat. No. 5,892,566 was issued to the present inventor on Apr. 6, 1999, and the contents thereof are hereby incorporated by reference. While curing many of the prior art deficiencies, the '566 patent nevertheless teaches video tracking of the eye as embedded in a visual presentation system which relies on either ambient light or light from the visual system to illuminate the eye. The problem with this system is that signals from the visual presentation system may be temporarily intermittent or be of such a limited bandwidth as to make illumination of the eye unreliable for the purpose of forming an image of the eye or its structures. Similar problems stem from reliance on ambient light for illumination. Thus, it is desirable to use a dedicated light source to illuminate the eye. The present inventor has discovered that best results are obtainable when the source of illumination has a wavelength that is different than that used for the visual presentation /stimulus, thereby rendering the illumination independent of the visual signal. Infra-red or an equivalent non-visible portion of the light spectrum has been found to be a preferred source of dedicated illumination.

Additionally, the physical and operational nature of known eye-tracking devices makes them unsuitable for use in many testing environments. For example, magnetic resonance imaging ("MRI") diagnosis equipment creates an environment which is makes it impossible to use known eye-tracking devices therein.

In operation, a typical MRI apparatus relies upon hydrogen protons which have a dipole movement and therefore behave as would a magnetic compass. In MRI scanning, the MRI apparatus operates as a large magnet wherein the protons align with the strong magnetic field but are easily disturbed by a brief radio frequency pulse of very low energy so as to alter their alignment. As the protons return to their orientation with the magnetic field, they release energy of a radio frequency that is strongly influenced by the biochemical environment. The released energy as detected and mathematically analyzed for display as a two dimensional proton density image according to the signal intensity of each issue.

The magnetic coils of the MRI apparatus are permanently fixed within a large structure so as to form a large magnet with a very confining entrance known as the bore. A patient is placed upon a scanner table that is integrated with the MRI apparatus and slid into the middle of the bore.

Eye tracking equipment used during MRI scanning must not interfere with the motion of an individual within the bore. Since the bore is a low-clearance area, eye tracking equipment used therein must be streamlined: bulky items simply will not fit. Preferably, the equipment is lightweight and worn by the patient to move with the patient within the MRI apparatus.

Additionally, eye tracking devices used during MRI scanning must transmit signals in a format that is not affected by the characteristic output of the MRI apparatus. Radio frequencies used by the MRI apparatus typically disrupt signal modulation. Known eye tracking devices are not suited for use in this environment: their signals will not be transmitted clearly.

Additionally, the inner area of the bore produces a magnetic field which will draw metal items when magnetized. Known eye-tracking devices include parts that are easily magnetized and are, as a result, not suitable for use with MRI equipment.

The Applicant was further issued U.S. Pat. No. 5,414,459 entitled Fiber Optic Video Glasses and Projection System which addressed the need for eye stimulation within an MRI apparatus. The '459 device being formed from a shape and material of construction that are suitable for use within an MRI environment without the need for additional shielding.

Thus, what is needed is an eye tracking device that includes advantages of the known devices, while addressing the shortcomings they exhibit. Accordingly, the eye tracking device should be impervious to magnetic environments and the output of MRI equipment. The device should not only indicate eye motion, but should also monitor pupil state. The device should be compact enough to monitor a patient located within the bore of MRI equipment and provide diagnostic feedback that allows comparison of eye movement and brain activity. Additionally, the device should be compatible with patient relaxation equipment used during an MRI session. Lastly, the device should include a dedicated light source to illuminate the eye which has a wavelength that is different than that used for the visual presentation/ stimulus, such as infrared illumination or the like, thereby rendering the illumination independent of the visual signal.

SUMMARY OF THE INVENTION

The instant invention is an eye-tracking system that analyzes the motion of an individual's eye. As will be seen, the system is especially well-suited for analyzing the eye movement of a patient undergoing diagnostic treatment within a magnetic resonance imaging apparatus.

The system employs a fiber optic image guide that forms an image utilizing the reflected light of a dedicated illumination source which utilizes a wavelength which is out-of-band from that used For the visual presentation or stimulus, e.g. IR or an equivalent non-visible portion of the light spectrum, and thus conveys a real-time image of an individual's eye to an included image conversion device. The conversion device, in turn, generates a digitized representation of the real-time eye image received from the fiber optic image guide. The image guide is adjustably secured to a pair of glasses that are worn by the tested individual during the diagnosis. The fiber-optic nature of the image guide makes it impervious to the radiation generated by the MRI device, allowing the image guide to transmit images with clarity.

The present eye-tracking system locates key reference points in the digitized eye image and compares the location of those points to the position of corresponding reference points located within a control image. This comparison is made by a computer interfaced with the conversion device. The computer is directed by software that analyzes the relative positions of these reference points. Based upon the analysis, the computer software provides diagnostic feedback.

Thus, it is an objective of the present invention to provide an eye tracking system that is impervious to the highly-magnetic and EMF-rich environment of a magnetic resonance imaging device.

It is also an objective of the present invention to provide an eye tracking system that may be combined with diagnostic or relaxation equipment within confined environments.

It is yet a further objective of the present invention to provide an eye tracking system that selectively provides a visual image of a patient's eye for archival and/or comparison purposes.

It is also an objective of the present invention to provide an eye tracking system that allows comparison of brain activity with resultant eye motion.

It is a further objective of the present invention to provide an eye tracking system that allows diagnostic analysis of eye response to visual and/or audio stimulation.

It is yet another objective of the present invention to provide an eye tracking system that provides diagnostic information related not only to eye motion, but to pupil state, as well.

It is yet an additional objective of the present invention to provide an eye tracking system that provides an improved image of the eye and its structures by including a source of illumination which is independent of the visual signal to provide reliable and repeatable illumination conditions.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE PREFERRED EMBODIMENT

Figure 1:
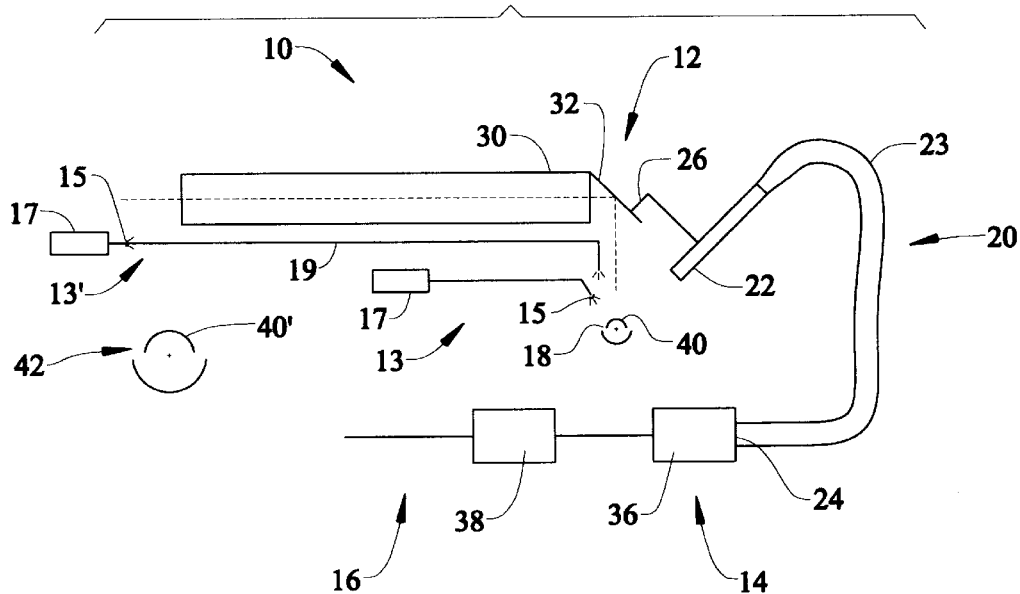
FIG. 1 is a pictorial view of the eye tracking device of the present invention.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown in the drawings and described in the specification.

Now with respect to FIG. 1, the fiber optic eye tracking system 10 of the present invention is shown. The present eye tracking system 10 includes three cooperative subsystems: an image converter subsystem 12, an image receiving subsystem 14, and an image processing subsystem 16. The image conveyor subsystem 12 delivers a real-time image of an individual's eye 18 to the image receiving subsystem 14. A source of out-of-band illumination is provided for obtaining an improved image of the eye and it's structures by including a source of illumination which is independent of the visual signal to provide reliable and repeatable illumination conditions. The out-of band light source may be provided as a direct local source 13, which includes an IR LED 15 electrically coupled to a power source 17 for generation of light therefrom and positioned proximate a selected region of the eye. Alternatively the power source, electrical coupling and IR source 13' may be remotely located and the out-of-band light is transmitted by coupling a fiber optic cable 19 to the output of the IR source and proximate a selected region near the eye as shown. The image receiving subsystem 14 creates a digital representation of the transferred real-time eye image. A copy of the original and digitized images may be stored for later use. As discussed below, stored images may be used as a control image. The digitized representation is then conveyed to the image processing subsystem. The image processing subsystem analyzes the digital representation and generates relevant feedback. Each of these subsystems 12,14,16 will be discussed more fully below.

Figure 2:
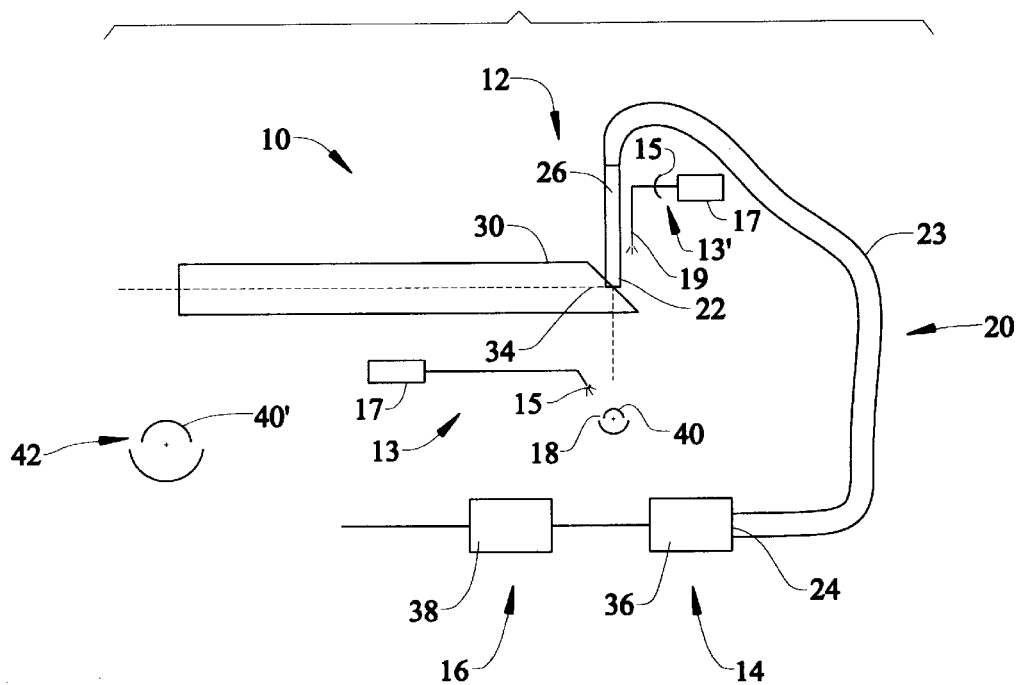
FIG. 2 is a pictorial view of the eye tracking device shown in FIG. 1, having an alternate fiber optic image guide mounting arrangement.
Figure 3:
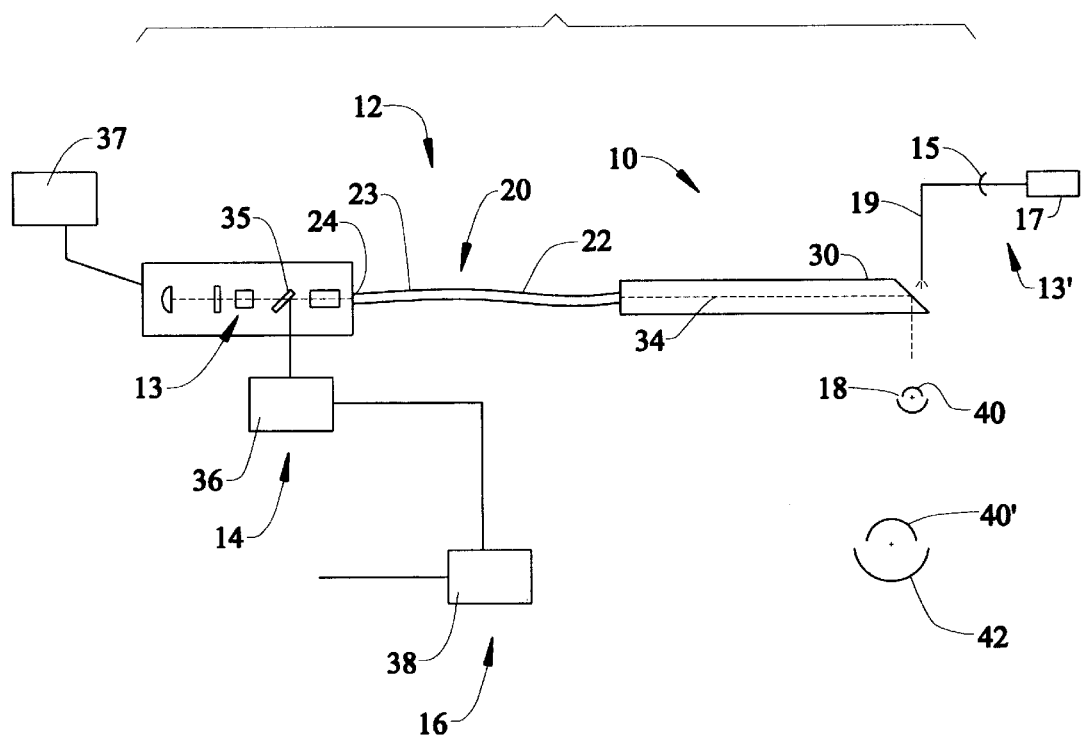
FIG. 3 is a pictorial view of the eye tracking device shown in FIG. 1, including a beam splitter that allows the fiber optic image guide to transmit information to and from an individual's eye.

The image conveyor subsystem 12 includes a flexible fiber optic image guide 20 having a first end 22 in optical communication with, a second end 24. The first end 22 and second end 24 are spaced apart by an image guide middle portion 23. The first end 22 of the fiber optic image guide 20 is directed at the patient's eye 18 during a MRI diagnosis session. The fiber optic image guide 20 includes a mounting bracket 26 that attaches the fiber optic image guide first end 22 to a pair of glasses 30 worn by the patient. In one embodiment, depicted in FIG. 1, the mounting bracket 26 removably attaches the fiber optic image guide 20 to the frame 32 of a pair of plastic glasses 30 worn by the diagnosed patient. This arrangement allows adjustable positioning of the fiber optic image guide first end 22. Because the fiber optic image guise 20 is adjustably attached to the frame 32 of the glasses 30, patient head motion advantageously does not adjust the relative positions of the patient's eye 18 and the fiber optic image guide first end 22. As a result, the patient's eye motion will still be tracked accurately, even if the patient moves his head. In an alternate embodiment, shown in FIG. 2, the mounting bracket 26 removably couples the fiber optic image guide 20 directly to a lens 34 in the glasses 30. A direct or remote source of out-of-band illumination 13,13' respectively, as described above, may be positioned as shown to utilize the same window utilized by the fiber optic image guide, and be positioned at the first end thereof. If a remote source is used, the fiber optic cable 19 may be coaxial with the image guide. The image conveyor subsystem 12 transmits a real-time eye image to the image receiving subsystem 14. As shown in FIG. 3, the image conveyor subsystem 12 includes a beam splitter 35 that allows the fiber optic image guide 20 simultaneously convey an eye image to the image receiving subsystem 14, while sending selected visual stimulation to the patient's eye 18. In this embodiment, the image conveyor subsystem 12 includes a video output device 37 interfaced with the fiber optic image guide 20 via the beam splitter 35.

The image receiving subsystem 14 includes a CCD video camera 36 interfaced with the fiber optic image guide second end 24. Because the fiber optic image guide first and second ends 22,24 are in optical communication, the fiber optic image guide first end 22 acts as a flexible lens extension for the CCD camera 36. As a result, the fiber optic image guide 20 conveys a real-time image from the fiber optic image guide first end 22, through the image guide middle section 23, to the fiber optic image guide second end 24 and, ultimately, to the CCD video camera 36. The CCD video camera 36 then digitizes the transferred image, creating a digital representation of the transmitted real-time image. The CCD video camera 36 forwards the resulting digital representation to the image processing subsystem 16.

Referring to FIG. 3, the image processing subsystem 16 includes a computer 38 interfaced with the CCD video camera 36. The computer 38 receives digital output from the CCD video camera 36 and performs operations directed by included computer software. More specifically, the CCD video camera 36 forwards a digital representation of the eye image to the computer 38, where the included software directs the computer to process the digitized image. In one embodiment, the software analyzes the digitized image of the eye and compares the location of a first reference point 40 therein, with the location of a corresponding second reference point 40' located in a control image. The control image may be a previously-stored image of the patient's eye 18 or some other suitable image. After comparing and tracking the location of corresponding reference points 40,40', the software produces diagnostic feedback. This feedback includes graphs, stimulus time/eye position charts, and a visual display of the current and/or control images of the eye 18. The feedback allows a technician to make patient assessments. An out-of-band light source 13, 13', may be advantageously incorporated herein by placement directly within the optical path (13) or possibly linked through a beam-splitter or similar device placed at the second end of the flexible fiber optic image guide (13').

Although the invention has been described in terms of a specific embodiment, it will be readily apparent to those skilled in this art that various modifications, rearrangements and substitutions can be made without departing from the spirit of the invention. The scope of the invention is defined by the claims appended hereto.

What is claimed is:

1. In an eye-tracking system for analyzing motion of an individual's eye, said system including a flexible fiber-optic image guide having a first end in optical communication with a second end, said first end positioned at a selected location with respect to said eye;

a camera operatively engaged with said second end of said fiber-optic image guide cable for conveying a real-time image of said eye, said camera adapted to produce a digitized representation of said real-time image of said eye; and a computer performing operations controlled by a software program for comparing the position of a first reference point disposed in said digital representation of said real-time image of said eye to the position of a corresponding second reference point disposed within a control image, said computer interfaced with said conversion means, the improvement comprising:

an independent illumination source constructed and arranged to illuminate the eye and its structures using a wavelength of light which is outside of the visible spectrum and effective to form a reflected image of the eye and its structures;

whereby reliable and repeatable illumination conditions are achieved.

2. The eye-tracking system of claim 1, including output means for generating feedback as a result of said processing.

3. The eye-tracking system of claim 1 including a mounting bracket sized and positioned to adjustably maintain said fiber-optic image guide first end at a selected position with respect to said individual's eye, whereby motion of an individual's head does not produce relative motion between said first end and said eye.

4. The eye tracking system of claim 1, wherein the independent illumination source uses an infrared wavelength of light.

5. The eye tracking system of claim 1, wherein the independent illumination source is a direct illumination source.

6. The eye tracking system of claim 1, wherein the independent illumination source is a remote illumination source.

7. The eye tracking system of claim 1, wherein the independent illumination source directly illuminates the eye.

8. The eye tracking system of claim 1, wherein the independent illumination source illuminates the eye through the flexible fiber optic image guide.

9. The eye tracking system of claim 8, wherein the independent illumination source is located at said first end of said flexible fiber optic image guide.

10. The eye tracking system of claim 8, wherein the independent illumination source is located at said second end of said flexible fiber optic image guide.

* * * * *